United States Patent
Takahashi et al.

(10) Patent No.: US 6,245,795 B1
(45) Date of Patent: *Jun. 12, 2001

(54) MELANOGENESIS INHIBITOR, SKIN COSMETIC COMPOSITION AND BATH PREPARATION

(75) Inventors: Yoshito Takahashi; Masaki Yoshida; Shintaro Inoue, all of Kanagawa (JP)

(73) Assignee: Kanebo, Limited, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/402,241

(22) PCT Filed: Mar. 26, 1998

(86) PCT No.: PCT/JP98/01389

§ 371 Date: Sep. 29, 1999

§ 102(e) Date: Sep. 29, 1999

(87) PCT Pub. No.: WO98/43672

PCT Pub. Date: Aug. 10, 1998

(30) Foreign Application Priority Data

Mar. 31, 1997 (JP) .................................................. 9-098154

(51) Int. Cl.[7] ........................ A61K 31/415; A61K 31/34; A61K 31/195
(52) U.S. Cl. ............................ 514/399; 514/471; 514/563
(58) Field of Search .................................. 514/471, 399, 514/563

(56) References Cited

U.S. PATENT DOCUMENTS 5,075,291 12/1991 DuRoss .
5,660,859 8/1997 Cody et al. .

FOREIGN PATENT DOCUMENTS

| 0 717 980 | 6/1996 | (EP) . |
| 57-46909 | 3/1982 | (JP) . |
| 63-196507 | 8/1988 | (JP) . |
| 11-65510 | 6/1989 | (JP) . |
| 2-17115 | 1/1990 | (JP) . |
| WO 93/20815 | 10/1993 | (WO) . |
| WO 97/16159 | 5/1997 | (WO) . |

OTHER PUBLICATIONS

Gros et al, Alteration of tyrosinase activity in human . . . , Melanoma Research, vol. 4, pp. 359–364, 1994.*
Ucar, Kalust, The effect of histamine . . . , Biochem. Biophy. Res. Commun. vol. 199/1, pp. 545–550, 1991.*
Tomita et al Histamine stimulate normal human melanocytes in vitro . . . , J. Dermatol. Sci. vol. 6/2, pp. 146–154, 1993.*
α–Melanocyte stimulating hormone and its analogue Nle[4]DPhe[7]α–MSH affect morphology, tyrosinase activity and melanogenesis in cultured human melanocytes, by Gillian Hunt et al, Journal of Cell Science 107, 205–211 (1994).
Abstracts From the 9th Annual Meeting of the Japanese Society for Pigment Cell Research, Pigment Cell Research 1994; 7:365–374 (2 pages).
Histamine stimulates normal human melanocytes in vitro: one of the possible inducers of hyperpigmentation in urticaria pigmentosa, by Yasushi Tomita et al, Journal of Dermatological Science 6 (1993) 146–154.
Endothelin–1 as a New Melanogen: Coordinated Expression of Its Gene and the Tyrosinase Gene in UVB–Exposed Human Epidermis, by Genji Imokawa et al, The Society for Investigative Dermatology, Inc., 1995, pp. 32–37.

* cited by examiner

Primary Examiner—William R. A. Jarvis
Assistant Examiner—Vickie Kim
(74) Attorney, Agent, or Firm—Flynn, Thiel, Boutell & Tanis, P.C.

(57) ABSTRACT

An object of the present invention is to provide a melanogenesis inhibitor and a skin cosmetic composition, which are superior in the effect of preventing pigmentation due to inflammation by selectively inhibiting stimulation of histamine to melanocytes.

The object is accomplished by containing a histamine $H_2$ receptor antagonist itself, cable of selectively blocking histamine $H_2$ receptors, or simultaneously containing the histamine $H_2$ receptor antagonist and at least one of histamine release inhibitors and histamine $H_3$ receptor agonists.

6 Claims, No Drawings

MELANOGENESIS INHIBITOR, SKIN COSMETIC COMPOSITION AND BATH PREPARATION

TECHNICAL FIELD

The present invention relates to a melanogenesis inhibitor, a skin cosmetic composition and a bath preparation, which are superior in effect of preventing pigmentation caused by inflammation of the skin due to ultraviolet rays or the like.

More particularly, the present invention relates to a melanogenesis inhibitor, a skin cosmetic composition and a bath preparation, which are used for the purpose of effectively inhibiting specific melanogenesis caused by stimulation of histamine released on inflammation of the skin, using histamine $H_2$ receptor antagonist antagonists.

BACKGROUND ART

Ultraviolet rays cause inflammation of the skin, resulting in the release of various factors, thereby stimulating melanocytes. Tyrosinase is activated in the stimulated melanocytes to produce melanin. This melanin is delivered to epidermal cells through dendrites extended by melanocytes due to stimulation, thereby melanizing the skin, while the melanin plays a role of absorbing ultraviolet rays to protect the body. However, excess accumulation of melanin causes pigmentation of the skin, such as stains, freckles or the like.

Heretofore, compounds capable of inhibiting a tyrosinase activity of melanocytes have exclusively been developed to inhibit pigmentation of the skin. Known examples thereof include ascorbic acid or derivatives thereof, placental extract, glycyrrhiza extract, hydroquinone or derivatives thereof, kojic acid and the like. Although these ingredients have an action of inhibiting the tyrosinase activity and inhibiting melanogenesis, almost all of them can not exert a sufficient effect because of low activity or causes a problem in safety. Therefore, there has been required the development of an effective and selective melanogenesis inhibitor having an action different from that of tyrosinase activity inhibition.

A method of blocking stimulation to melanocytes has been hitherto known as a technology of inhibiting melanogenesis by an action other than that of tyrosinase activity inhibition. A principal substance that stimulates melanocytes to accelerate melanogenesis in the skin inflamed by ultraviolet rays includes, for example, melanocyte stimulating hormone (MSH), endothelin-1 (ET-1), histamine or the like (see Journal of Cell Science, Vol. 107, page 205, 1994; The Journal of Investigative Dermatology, Vol. 105, page 32, 1995; and Journal of Dermatological Science, Vol. 6, page 146, 1993). Among them, MSH and ET-1 are known to stimulate melanocytes via specific receptors. In particular, inhibition of melanogenesis by means of a method of inhibiting binding to the receptors has been reported for ET-1 (see Pigment Cell Research, Vol. 7, page 373, 1994).

Of course ET-1 is an effective ingredient, however, it is considered to be important to prevent stimulation due to histamine which particularly closely relates to the inflammatory reaction, considering the prevention of pigmentation after inflammation of the skin.

It has commonly been known that histamine is a substance, which is released from mast cells due to various stimulations and has various physiological activities, and includes three specific receptors ($H_1$, $H_2$ and $H_3$). It is considered that an $H_1$ receptor mainly relates an immediate anaphylactic reaction (allergic reaction), an $H_2$ receptor mainly relates to secretion of gastric acid, and an $H_3$ receptor relates to a release or synthesis of histamine in mast cells.

With regard to melanogenesis due to histamine stimulation in melanocytes, however, there was no established theory about the fact whether or not melanogenesis is caused by the reaction via a receptor specific for histamine. Therefore, histamine-mediated melanogenesis has never been made clear. Furthermore, there has hitherto been submitted a report disclosing a whitening effect of an antihistaminic agent, particularly histamine $H_1$ receptor antagonist (Japanese Published Unexamined Patent Application No.17115/1990), but the histamine $H_1$ receptor antagonists do not have an effect of inhibiting melanogenesis as described hereinafter.

DISCLOSURE OF THE INVENTION

Under these circumstances, we have intensively studied to selectively inhibit a melanogenesis acceleration action of histamine. As a result, surprisingly, we have found a new fact that histamine stimulates melanocytes via its specific receptor to accelerate melanogenesis and, moreover, the melanogenesis is accelerated only via $H_2$ receptors without being concerned with $H_1$ and $H_3$ receptors. Thus, the present invention has been completed. It is an object of the present invention to provide a melanogenesis inhibitor, a skin cosmetic composition and a bath preparation, which are superior in the effect of preventing pigmentation due to inflammation by selectively inhibiting stimulation of histamine to melanocytes.

The above-mentioned object can be attained by a melanogenesis inhibitor comprising a histamine $H_2$ receptor antagonist capable of selectively inhibiting a histamine $H_2$ receptor, and a skin cosmetic composition and a bath preparation, comprising a histamine $H_2$ receptor antagonist; or a melanogenesis inhibitor comprising a histamine $H_2$ receptor antagonist, and at least one of histamine release inhibitors and histamine $H_3$ receptor agonists, and a skin cosmetic composition and a bath preparation, comprising a histamine $H_2$ receptor antagonist, and at least one of histamine release inhibitors and histamine $H_3$ receptor agonists.

BEST MODE FOR CARRYING OUT THE INVENTION

The present invention will be described in detail hereinafter.

The histamine $H_2$ receptor antagonist used in the present invention includes, for example, cimetidine, famotidine, ranitidine hydrochloride, tiotidine, zolantidine, metiamide, burimamide, nizatidine, etc.; inorganic acid salts thereof, such as hydrochloride, hydrobromide, sulfate, etc.; organic acid salts thereof, such as fumarate, maleate, etc.; and a mixture thereof.

The histamine $H_2$ receptor antagonist used in the present invention may be alone, or two or more kinds of them can be appropriately selected.

In order to supplement the action of the histamine $H_2$ receptor antagonist or to make it effective, a release inhibitor of histamine to be released from mast cells (antiallergic drug) and a histamine $H_3$ receptor agonist for inhibiting synthesis or release of histamine of mast cells can also be used, simultaneously.

The histamine release inhibitor used in the present invention includes, for example, emedastine hydrochloride, emedastine fumarate, tranilast, sodium cromoglicate, azelastine hydrochloride, terfenadine, and plant extracts, such as a solvent extract of a plant belonging to the genus Rosaceae Pyracantha.

The histamine $H_3$ receptor agonist used in the present invention includes, for example, R-(α)-methylhistamine or the like.

The melanogenesis inhibitor of the present invention may be one of the above-mentioned substances, and may also contain solvents such as water or vehicles.

For example, the melanogenesis inhibitor of the present invention can be incorporated into skin cosmetic compositions such as cosmetics and quasi-drugs, and bath preparations, because of its excellent melanogenesis inhibition effect. In addition, the melanogenesis inhibitor can also be used as pharmaceuticals, and reagents for studying and testing to be added in the cultured cell system.

The amount of the melanogenesis inhibitor of the present invention to be incorporated into the skin cosmetic composition or bath preparation varies depending on the subjects to which it is to be applied and is not defined unconditionally, but the amount on a dry basis of each substance is preferably from 0.0001 to 10% by weight, more preferably from 0.001 to 5% by weight, based on the total amount of the composition to be applied.

If necessary, fats and oils, humectants, pigments, dyes, surfactants, antioxidants, UV absorbers, antiseptics, water-soluble polymers and resins, which are conventionally incorporated into pharmaceuticals, quasi-drugs, skin external preparations such as cosmetics, and bath preparations, can be appropriately incorporated into the skin cosmetic composition or bath preparation of the present invention.

It is possible for the invention to take any dosage form such as ointments, lotions, milky lotions, creams, packs, granules, injections, etc. depending on the subjects to which it is to be applied.

The melanogenesis inhibitor of the present invention can be suitably used for prevention or treatment of diseases to which the melanogenesis inhibitor is usually applied, e.g. superpigmentation such as freckles, lentigo, and secondary diseases after inflammation, because of its excellent melanogenesis inhibition action as described hereinafter.

The dose of the melanogenesis inhibitor of the present invention varies depending on the symptoms, weight or age of the patient, kind of histamine $H_2$ receptor antagonist as an active ingredient, kind of histamine release inhibitor and/or histamine $H_3$ receptor agonist to be incorporated appropriately, and dosage form, but is usually administered orally or parenterally 1 or several times per day with a proper dose (0.01 to 10 mg/kg).

When the melanogenesis inhibitor of the present invention is parenterally administered, clinically used injections such as ranitidine hydrochloride, famotidine, etc. can also be used, but external preparations such as ointments, creams, liquid preparations, etc. are preferably used. The external preparation is applied or rubbed on the affected part 1 or several times per day with a proper dose, and is appropriately controlled according to conditions of the disease.

Any of these external preparations can be produced easily by a conventional method and the amount of the histamine $H_2$ receptor antagonist to be incorporated into these external preparations varies depending on the subjects to which it is to be applied and is not defined unconditionally, but the amount on a dry basis of each substance is preferably from 0.01 to 10% by weight, based on the total amount of the composition to be applied. Furthermore, the amount of the histamine release inhibitor and/or histamine $H_3$ receptor agonist to be appropriately incorporated also varies depending on the subjects to which it is to be applied and is not defined unconditionally, but the amount on a dry basis of each substance is preferably from 0.005 to 15% by weight, based on the total amount of the composition to be applied.

When the melanogenesis inhibitor of the present invention is orally administered, oral preparations of various histamine $H_2$ receptor antagonists such as cimetidine, ranitidine hydrochloride, famotidine, nizatidine and the like used clinically can also be used as they are.

As described above, it is clear that, according to the present invention, there can be provided a melanogenesis inhibitor, which is superior in function of selectively inhibiting stimulation of histamine to melanocytes without causing any serious side effects thereby to prevent pigmentation due to inflammation, by using a receptor antagonist capable of selectively blocking a histamine $H_2$ receptor. It is also clear that a skin cosmetic composition and a bath preparation, containing the compound, can also be provided.

As the examples for making the effect of the melanogenesis inhibition action according to the present invention clear, the following Comparative Examples and Examples will be illustrated.

TEST EXAMPLE 1

Observation of Morphological Change of Melanocytes

A change of melanocytes due to stimulation of each test sample was estimated utilizing melanization of melanocytes and extension of dendrites due to melanogenesis as an index. The procedure was as follows.

Cultured normal human melanocytes were inoculated into a 12 wells-plastic plate at a concentration of $5 \times 10^4$ cells/well and cultured at 37° C. for 72 hours under 5% $CO_2$ and saturated steam (the following cultures were carried out under the same conditions). Each test sample (Comparative Examples 1 to 5 and Example 1 shown in Table 1) was added to the well and, after culturing for 48 hours, the morphological change of the melanocytes was observed by using a phase-contrast microscope.

Furthermore, the medium used was MCDB 153 HAA medium, to which 5 μg/ml of insulin, 0.1 ng/ml of epidermal growth factor, 1 ng/ml of basic fibroblast growth factor and 0.5 mM of calcium chloride were respectively added at a final concentration.

The results are shown in Table 1.

TABLE 1

| Samples to be added | Melanization of cells | Extension of dendrite |
| --- | --- | --- |
| No addition (Comparative Example 1) | − | − |
| 1 μM Histamine (Comparative Example 2) | + | + |
| 1 μM Histamine 30 μM Chlorpheniramine($H_1$ receptor antagonist) (Comparative Example 3) | + | + |
| 1 μM Histamine 30 μM Thioperamide ($H_3$ receptor antagonist) (Comparative Example 4) | + | + |
| 10 μM Dimaprit ($H_2$ receptor agonist) (Comparative Example 5) | + | + |

TABLE 1-continued

| Samples to be added | Melanization of cells | Extension of dendrite |
|---|---|---|
| $\mu$M Histamine<br>30 $\mu$M Ranitidine (H$_2$ receptor antagonist)<br>(Example 1) | – | – |

Note
+: observed
–: not observed

As a result of the addition of histamine (Comparative Example 2), the melanization and extension of the dendrites were observed in the cultured normal human melanocytes. This change was inhibited only when the H$_2$ receptor antagonist (Example 1) among each receptor antagonist for histamine was simultaneously added. The same change as in case of adding histamine was also observed as a result of the addition of the histamine H$_2$ receptor agonist (Comparative Example 5). As is apparent from the above results, histamine stimulates melanocytes via H$_2$ receptors.

TEST EXAMPLE 2

Melanogenesis Inhibition Test (Measurement of Tyrosinase Activity)

A quantitative melanogenesis inhibition test using melanocytes was carried out by measuring the tyrosinase activity in the melanocytes. The procedure was as follows.

Cultured normal human melanocytes were inoculated into a 12 wells-plastic plate at a concentration of 1.2×10$^5$ cells/well and cultured at 37° C. for 72 hours under 5% CO$_2$ and saturated steam (the following cultures were carried out under the same conditions). Each test sample (Comparative Examples 6 to 8 and Example 2 shown in Table 2) was added to the well and, after culturing for 24 hours, 261 mCi/mg of L-[3,5-$^3$H]tyrosine was added in an amount of 1 $\mu$Ci/well of the plate and the plate was further cultured for 36 hours. After the completion of the culture, the same amount of an aqueous solution containing 10% trichloroacetic acid and 20% activated charcoal was added to the supernatant fluid and the mixture was cooled at 4° C. for 15 minutes. Then, the activated charcoal was removed by centrifugation. This operation was further repeated twice, and the radioactivity of the resulting solution was measured. The culture medium used is the same as in Test Example 1.

The results are shown in Table 2. The lower the relative radioactivity, the lower the tyrosinase activity becomes.

TABLE 2

| Samples to be added | Relative radioactivity |
|---|---|
| No addition (Comparative Example 6) | 100 ± 26 |
| 1 $\mu$M Histamine (Comparative Example 7) | 223 ± 14 |
| 10 $\mu$M Dimaprit (H$_2$ receptor agonist) (Comparative Example 8) | 187 ± 27 |
| 1 $\mu$M Histamine<br>30 $\mu$M Ranitidine (H$_2$ receptor antagonist) (Example 2) | 115 ± 16 |

As is apparent from the results of Table 2, melanogeneis, accelerated by histamine, is inhibited by the histamine H$_2$ receptor antagonist (Example 2).

Examples such as melanogenesis inhibitor, skin cosmetic composition containing the same, and bath preparation of the present invention will be illustrated hereinafter, but the present invention is not limited thereto.

EXAMPLES 3 TO 5

Liquid Preparation

| Formulation (% by weight) | Example 3 | Example 4 | Example 5 |
|---|---|---|---|
| Famotidine | 0.02 | 0.02 | 0.02 |
| Azelastine hydrochloride | 0 | 0.01 | 0.05 |
| R-($\alpha$)-methylhistamine | 0 | 0 | 0.05 |
| Sucrose | 60.0 | 60.0 | 60.0 |
| Ethyl parahydroxybenzoate | 0.02 | 0.02 | 0.02 |
| Propyl parahydroxybenzoate | 0.01 | 0.01 | 0.01 |
| Purified water | bal. | bal. | bal. |
| Total | 100 | 100 | 100 |

The above-mentioned respective ingredients were dissolved in purified water and the mixture homogenized with stirring to prepare a liquid preparation.

EXAMPLES 6 TO 9

Cream

| | Formulation (% by weight) | Example 6 | Example 7 | Example 8 | Example 9 |
|---|---|---|---|---|---|
| A | Cetanol | 3 | 3 | 3 | 3 |
| | Glyceryl monostearate | 2.5 | 2.5 | 2.5 | 2.5 |
| | Polyoxyethylene cetyl ether (20 E.O.) | 1.5 | 1.5 | 1.5 | 1.5 |
| | Liquid paraffin | 10 | 10 | 10 | 10 |
| | Glyceryl tri-2-ethylhexanoate | 5 | 5 | 5 | 5 |
| | Methylpolysiloxane | 1 | 1 | 1 | 1 |
| B | Butyl parahydroxy-benzoate | 0.1 | 0.1 | 0.1 | 0.1 |
| C | Methyl parahydroxy-benzoate | 0.15 | 0.15 | 0.15 | 0.15 |
| | Disodium edetate | 0.1 | 0.1 | 0.1 | 0.1 |
| | Cimetidine | 0.01 | 0.01 | 0.01 | 0.01 |
| | Ranitidine hydrochloride | 0 | 0.01 | 0 | 0.01 |
| | Tranilast | 0 | 0 | 0.01 | 0.005 |
| D | Na N-stearoyl-L-glutamate | 0.9 | 0.9 | 0.9 | 0.9 |
| | Dipropylene glycol | 5 | 5 | 5 | 5 |
| | Purified water | bal. | bal. | bal. | bal. |
| | Total | 100 | 100 | 100 | 100 |

The ingredient (A) was homogeneously mixed and dissolved at 80° C., and the resulting mixture and the ingredient (B) were mixed and dissolved (mixed solution I). Separately, the ingredient (D) was homogeneously mixed and dissolved at 80° C., and the resulting mixture and the ingredient (C) were mixed and dissolved (mixed solution II). Then, the mixed solution II was added gradually to the mixed solution I and the mixture was cooled to 30° C. with sufficiently stirring to obtain a cream.

EXAMPLES 10 TO 13

Lotion

| Formulation (% by weight) | Example 10 | Example 11 | Example 12 | Example 13 |
|---|---|---|---|---|
| Ethanol | 5 | 5 | 5 | 5 |
| Glycerin | 5 | 5 | 5 | 5 |
| Polyoxyethylene hydrogenated castor oil (60 E.O.) | 0.5 | 0.5 | 0.5 | 0.5 |
| Methylparaben | 0.02 | 0.02 | 0.02 | 0.02 |
| Perfume | 0.05 | 0.05 | 0.05 | 0.05 |
| Metiamide | 0.1 | 0.1 | 0.1 | 0.1 |
| Sodium cromoglicate | 0 | 0.02 | 0 | 0.01 |
| R-(α)-methylhistamine | 0 | 0 | 0.02 | 0.01 |
| Purified water | bal. | bal. | bal. | bal. |
| Total | 100 | 100 | 100 | 100 |

The respective ingredients were mixed and dissolved to prepare a lotion.

EXAMPLES 14 TO 17

Bath Preparation

| Formulation (% by weight) | Example 14 | Example 15 | Example 16 | Example 17 |
|---|---|---|---|---|
| Sodium sulfate | 85 | 85 | 85 | 85 |
| Perfume and surfactant | q.s. | q.s. | q.s. | q.s. |
| Organic dye | q.s. | q.s. | q.s. | q.s. |
| Burimamide | 1 | 1 | 1 | 1 |
| Emedastine hydrochloride | 1 | 0 | 0.5 | 1 |
| Terfenadine | 0 | 1 | 0.5 | 1 |
| Sodium bicarbonate | bal. | Bal. | bal. | bal. |
| Total | 100 | 100 | 100 | 100 |

The respective ingredients were mixed to prepare a bath preparation. About a 3,000-fold dilution of this bath preparation was made before use.

EXAMPLES 18 TO 22

Ointment

| | Formulation (% by weight) | Example 18 | Example 19 | Example 20 | Example 21 | Example 22 |
|---|---|---|---|---|---|---|
| A | Squalane | 4.7 | 4.7 | 4.7 | 4.7 | 4.7 |
| | White soft paraffin | 24 | 24 | 24 | 24 | 24 |
| | Stearyl alcohol | 8.7 | 8.7 | 8.7 | 8.7 | 8.7 |
| | Isopropyl myristate | 6 | 6 | 6 | 6 | 6 |
| | Polyethylene glycol monostearate | 1.3 | 1.3 | 1.3 | 1.3 | 1.3 |
| | Polyoxyethylene alkyl ether phosphate | 2.3 | 2.3 | 2.3 | 2.3 | 2.3 |
| | Glyceryl monostearate | 2 | 2 | 2 | 2 | 2 |
| | Butyl parahydroxy-benzoate | 0.1 | 0.1 | 0.1 | 0.1 | 0.1 |
| B | Methyl parahydroxy-benzoate | 0.1 | 0.1 | 0.1 | 0.1 | 0.1 |
| | Propylene glycol | 6.7 | 6.7 | 6.7 | 6.7 | 6.7 |
| | Ranitidine hydrochloride | 0.01 | 0.1 | 0.01 | 0.1 | 1 |
| | Solvent extract of plant belonging to the genus Rosaceae Pyracantha | 0 | 0 | 15 | 15 | 0 |
| | Purified water | bal. | bal. | bal. | bal. | bal. |
| | Total | 100 | 100 | 100 | 100 | 100 |

The respective ingredients of (B) were mixed with heating in a hot bath at 80° C. and the resulting mixture was gradually added to a mixture of the respective ingredients of (A) heated to 80° C. Then, the respective ingredients were sufficiently emulsified and dispersed by vigorously stirring (2500 rpm) with a homogenizer for 2.5 minutes, followed by gradual cooling with stirring to obtain an ointment.

What is claimed is:

1. In a method of inhibiting the development of melanogenesis in a subject in need of this type of inhibition, the improvement comprising administering to said subject a composition containing a pharmacologically effective amount of a histamine $H_2$ receptor antagonist.

2. The method of claim 1, wherein said composition additionally comprises a histamine $H_3$ receptor agonist.

3. The method of claim 1, wherein said composition is applied to the subject externally.

4. The method of claim 1, wherein said histamine $H_2$ receptor antagonist is present in an amount of from 0.0001 to 10 wt. %.

5. The method of claim 1, wherein said composition is a skin cosmetic composition.

6. The method of claim 1, wherein said composition is a bath preparation composition.

* * * * *

UNITED STATES PATENT AND TRADEMARK OFFICE
CERTIFICATE OF CORRECTION

PATENT NO. : 6,245,795 B1
DATED : June 12, 2001
INVENTOR(S) : Yoshito Takahashi et al.

It is certified that error appears in the above-identified patent and that said Letters Patent is hereby corrected as shown below:

Title page,
Item [83], replace PCT Pub. Date: "Aug. 10, 1998" with -- October 8, 1998 --.

Signed and Sealed this

First Day of January, 2002

*Attest:*

JAMES E. ROGAN
*Attesting Officer*  *Director of the United States Patent and Trademark Office*